US009260378B2

(12) United States Patent
Lui et al.

(10) Patent No.: US 9,260,378 B2
(45) Date of Patent: Feb. 16, 2016

(54) PROCESS FOR THE PREPARATION OF SUBSTITUTED N-(BENZYL)CYCLOPROPANAMINES BY IMINE HYDROGENATION

(75) Inventors: Norbert Lui, Odenthal (DE); Wahed Ahmed Moradi, Monheim (DE); Thomas Norbert Muller, Monheum (DE)

(73) Assignee: BAYER INTELLECTUAL PROPERTY GMBH (DE)

( * ) Notice: Subject to any disclaimer, the term of this patent is extended or adjusted under 35 U.S.C. 154(b) by 0 days.

(21) Appl. No.: 13/883,241

(22) PCT Filed: Nov. 4, 2011

(86) PCT No.: PCT/EP2011/069426
§ 371 (c)(1),
(2), (4) Date: May 2, 2013

(87) PCT Pub. No.: WO2012/059585
PCT Pub. Date: May 10, 2012

(65) Prior Publication Data

US 2013/0217910 A1 Aug. 22, 2013

Related U.S. Application Data

(60) Provisional application No. 61/410,517, filed on Nov. 5, 2010.

(30) Foreign Application Priority Data

Nov. 5, 2010 (EP) .................................... 10190077

(51) Int. Cl.

| | |
|---|---|
| ***C07C 209/52*** | (2006.01) |
| ***C07C 211/35*** | (2006.01) |
| ***C07C 213/02*** | (2006.01) |
| ***C07C 227/04*** | (2006.01) |
| ***C07C 251/24*** | (2006.01) |
| ***C07C 217/58*** | (2006.01) |

(52) U.S. Cl.
CPC ............. *C07C 209/52* (2013.01); *C07C 211/35* (2013.01); *C07C 213/02* (2013.01); *C07C 217/58* (2013.01); *C07C 227/04* (2013.01); *C07C 251/24* (2013.01); *C07C 2101/02* (2013.01)

(58) Field of Classification Search
CPC .. C07C 251/24; C07C 209/52; C07C 211/35; C07C 213/02; C07C 227/04; C07C 217/56; C07C 229/38; C07C 2101/02; C07C 217/58
USPC ..................... 560/48; 564/384, 385, 387, 389
See application file for complete search history.

(56) References Cited

U.S. PATENT DOCUMENTS

| | | | | |
|---|---|---|---|---|
| 3,083,226 | A * | 3/1963 | Horrom et al. | 560/27 |
| 3,153,093 | A | 10/1964 | Horrom | |
| 7,435,815 | B2 | 10/2008 | Aissaoui et al. | 546/1 |
| 2008/0076751 | A1 | 3/2008 | Aslanian et al. | 514/210.02 |
| 2008/0089858 | A1 | 4/2008 | McKittrick et al. | 424/85.2 |
| 2010/0041628 | A1 | 2/2010 | Enomoto et al. | 514/64 |
| 2015/0094492 | A1* | 4/2015 | Himmler et al. | 564/384 |

FOREIGN PATENT DOCUMENTS

| | | | |
|---|---|---|---|
| EP | 2119703 | A1 | 11/2009 |
| JP | 2006-502209 | | 1/2006 |
| JP | 2010-503677 | | 2/2010 |
| WO | WO 2004/033418 | A2 | 4/2004 |
| WO | WO 2008/033456 | | 3/2008 |
| WO | WO 2008/033464 | A2 | 3/2008 |

OTHER PUBLICATIONS

Bumgardner ("Hydride Reduction of N-Cyclopropylimines" Journal of Organic Chemistry, vol. 37, No. 3, 1972, p. 407-409).*

International Search Report issued Dec. 14, 2011 in corresponding International Application No. PCT/EP2011/069426.

Bowman, W.R., et al.: "Generation of Aminyl Radicals using Sulfenamides as Synthetic Precursors", *Tetrahedron*, vol. 50, No. 4, Jan. 1, 1994, pp. 1275-1294, Elsevier Science Ltd, printed in Great Britain, ISSN: 0040-4020/94, DOI:10.1016/S0040-4020(01)80837-1, p. 1283, last paragraph-p. 1284, line 5.

Nagasawa, H.T., et al.: "Latent Inhibitors of Aldehyde Dehydrogenase as Alcohol Deterrent Agents", *Journal of Medicinal Chemistry*, vol. 27, No. 10., 1984, pp. 1335-1339, XP002631589, American Chemical Society, Washington, DC, ISSN: 0022-2623, p. 1338, right-hand column, line 15-line 22.

Tripathi, R.P., et al.: "Synthesis and antitubercular activity of substituted phenylmethyl- and pyridylmethyl amines", *Bioorganic & Medicinal Chemistry*, vol. 14, No. 24, Dec. 15, 2006, pp. 8186-8196, XP025133654, ISSN: 0968-0896, DOI:10.1016/J.BMC.2006.09.020, p. 8187, fig. 1, example 1.

(Continued)

*Primary Examiner* — Jafar Parsa
*Assistant Examiner* — Amy C Bonaparte
(74) *Attorney, Agent, or Firm* — Ostrolenk Faber LLP

(57) ABSTRACT

The present invention relates to a process for the preparation of substituted N-(benzyl)cyclopropanamines of the general formula (II) starting from N-[(aryl)methylene]cyclopropanamine derivatives. The present invention further provides the N-[(aryl)methylene]cyclopropanamine derivatives used as starting compounds in this process according to the invention, and their use for the preparation of substituted N (benzyl) cyclopropanamines.

(II)

Z
N
H
$(X)_n$

12 Claims, No Drawings

(56) References Cited

OTHER PUBLICATIONS

Dilman, A.D., et al.: "Trifluoromethylation of Salicyl Aldimines", *J. Org. Chem*, vol. 72, No. 22, 2007, pp. 8604-8607, XP002631590, American Chemical Society, Washington, D.C., ISSN: 0022-3263, p. 8606, example 6, table 3.

Vukics, K., et al.: "Synthesis of C-Aryl-N-cyclopropylnitrones", *Synthetic Communications*, vol. 33, No. 19, pp. 3419-3425, 2003, XPOO2631591, ISSN: 0039-7911, p. 3420, last paragraph; DOI: 10.1081/SCC-120024001.

E.M. Smith et al., Bioorganic & Medicinal Chemistry Letters, Jun. 8, 2010, vol. 20, 2010, pp. 4602-4606.

Pan Li et al., "Solvent- and Catalyst-free Synthesis and Antifungal Activities of α-Aminophosphonate Containing Cyclopropane Moiety", Chemical Research in Chinese Universities, 2010, vol. 26, No. 3, pp. 389-393.

* cited by examiner

PROCESS FOR THE PREPARATION OF SUBSTITUTED N-(BENZYL)CYCLOPROPANAMINES BY IMINE HYDROGENATION

CROSS REFERENCE TO RELATED APPLICATION(S)

The present application is a 35 U.S.C. §371 national phase conversion of PCT/EP2011/069426 filed on Nov. 4, 2011, which claims priority to European Application No. 10190077.7 filed on Nov. 5, 2010 and U.S. Provisional Application No. 61/410,517 filed on Nov. 5, 2010. Applicants claim priority to the foregoing patent applications. The PCT International Application was published in the English language.

The present invention relates to a process for the preparation of substituted N-(benzyl)cyclopropanamines of the general formula (II) starting from N-[(aryl)methylene]cyclopropanamine derivatives. The present invention further provides the N-[(aryl)methylene]cyclopropanamine derivatives used as starting compounds in this process according to the invention and also their use for the preparation of substituted N-(benzyl)cyclopropanamines.

Substituted N-(benzyl)cyclopropanamines are important intermediates for the manufacture of agrochemical active ingredients. Correspondingly substituted N-(benzyl)cyclopropanamines are described, for example, in the synthesis of fungicidally effective pyrazolecarboxamides (cf. e.g. WO 2007/087906, PCT/EP2010/056521). It is known that N-(phenylmethylene)cyclopropanamine can be reduced with sodium cyanoborohydride to give N-benzyl-cyclopropanamine (see *J. Lab. Comp. Radiopharm.* 1981, 18, 781-90 and *J. Org. Chem.* 2000, 65, 96-103). A disadvantage of this process is high costs of sodium cyanoborohydride. In WO 2006/066896, sodium triacetoxyboro-hydride is used instead of sodium cyanoborohydride. In *Synthetic Commun.* 2003, 33, 3419-3425, only borohydride in methanol is used. Here too, the costs are too high. A further process, the alkylation of cyclopropylamine with benzyl bromide, is described in *Bioorg. Med. Chem.* 2006, 14, 8506-8518. Here, the yield following complex chromatography is only 48%. In the case alkylation with benzyl bromide, the possible polyalkylation also takes place. *Tetrahedron* 2008, 64, 11783-11788 describes the preparation of N-monosubstituted benzylamines with hydrogen and palladium on carbon in chloroform. This gives the hydrochloride. A disadvantage of this process is the use of toxic chloroform and corrosion problems on account of the acidic hydrogenation. The hydrogenolysis of cyclopropyl groups to the corresponding n-propyl or isopropyl derivatives in the presence of hydrogenation catalysts even under mild conditions is generally known and adequately described (cf. Rylander "Catalytic Hydrogenation in Organic Syntheses", pages 251 to 259, Academic Press, New York, 1979 and Nishimura "Handbook of Heterogeneous Catalytic Hydrogenation for Organic Synthesis", pages 640 to 647, John Wiley & Sons, New York, 2001). A particular example of undesired hydrogenolysis of a cyclopropyl ring in the presence of palladium on carbon at a hydrogen pressure of 1 bar and room temperature is described in *Chem. Eur.* 1 1997, 3, 1370-1374.

Proceeding from this prior art, the object of the present invention is to provide an alternative process for the preparation of substituted N-(benzyl)cyclopropanamines which can preferably be carried out easily and cost-effectively. The substituted N-(benzyl)cyclopropanamines obtainable using this desired process should preferably be obtained with high yield and high purity. In particular, the desired process should allow the desired target compounds to be obtained without the need for complex purification methods.

This object is achieved by a novel process for the preparation of substituted N-(benzyl)cyclopropanamines.

The process (A) according to the invention is characterized in that N-[(aryl)methylene]cyclopropanamine derivatives of the general formula (I)

(I)

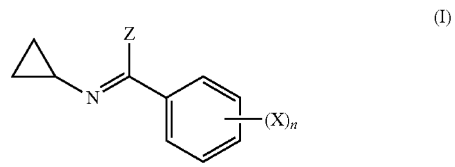

in which

Z is hydrogen, $C_1$-$C_8$-alkyl, $C_1$-$C_4$-haloalkyl or $C_3$-$C_7$-cycloalkyl, X is halogen, cyano, hydroxyl, $C_1$-$C_8$-alkyl, $C_1$-$C_8$-haloalkyl having up to 9 identical or different halogen atoms, $C_1$-$C_8$-alkylamino, di($C_1$-$C_8$-alkyl)amino, $C_1$-$C_8$-alkoxy, $C_1$-$C_8$-haloalkoxy having up to 9 identical or different halogen atoms, $C_1$-$C_8$-alkoxy-$C_1$-$C_8$-alkyl; $C_1$-$C_8$-alkylsulphanyl, $C_1$-$C_8$-haloalkylsulphanyl having up to 9 identical or different halogen atoms, $C_3$-$C_7$-cycloalkyl, ($C_3$-$C_7$-cycloalkyl)-$C_1$-$C_8$-alkyl, $C_3$-$C_7$-halocycloalkyl having up to 9 identical or different halogen atom, formyl, fonnyloxy, fonnylamino, carboxy, carbamoyl, N-hydroxycarbamoyl, carbamates, ($C_1$-$C_8$-alkyl)carbonyl, ($C_1$-$C_8$-haloalkyl)carbonyl having up to 9 identical or different halogen atoms, $C_1$-$C_8$-alkylcarbamoyl, di($C_1$-$C_8$-alkyl)carbamoyl, N-($C_1$-$C_8$-alkyloxy)carbamoyl, ($C_1$-$C_8$-alkoxy)carbamoyl, N-$C_1$-$C_8$-alkyl-($C_1$-$C_8$-alkoxy)carbamoyl, ($C_1$-$C_8$-alkoxy)-carbonyl, ($C_1$-$C_8$-haloalkoxy)carbonyl having up to 9 identical or different halogen atoms, ($C_1$-$C_8$-akylamino)carbonyl, di($C_1$-$C_8$-alkylamino)carbonyl, ($C_1$-$C_8$-alkyl)carbonyloxy, ($C_1$-$C_8$-haloalkyl)carbonyloxy having up to 9 identical or different halogen atoms, ($C_1$-$C_8$-alkyl) carbonylamino, ($C_1$-$C_8$-haloalkyl)-carbonylamino having up to 9 identical or different halogen atoms, ($C_1$-$C_8$-alkylamino)carbonyloxy, di-($C_1$-$C_8$-alkylamino)carbonyloxy, ($C_1$-$C_8$-alkyloxy)carbonyloxy, $C_1$-$C_8$-alkylsulphenyl, $C_1$-$C_8$-haloalkylsulphenyl having up to 9 identical or different halogen atoms, $C_1$-$C_8$-alkylsulphinyl, $C_1$-$C_8$-haloalkylsulphinyl having up to 9 identical or different halogen atoms, $C_1$-$C_8$-alkylsulphonyl, $C_1$-$C_8$-haloalkylsulphonyl having up to 9 identical or different halogen atoms, tri($C_1$-$C_8$-alkyl)silyl, tri($C_1$-$C_8$-alkyl)silyl-$C_1$-$C_8$-alkyl, moreover two substituents X can form a 5- or 6-membered ring, which may be saturated or unsaturated and optionally also comprises heteroatoms, n is 1, 2, 3, 4 or 5, are catalytically hydrogenated, thus obtaining the N-(benzyl) cyclopropanamines of the general formula (II)

(II)

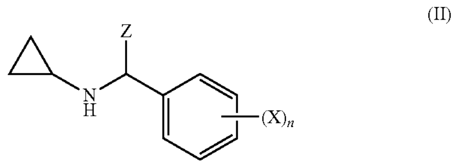

in which Z, X and n have the meanings given above.

Preferred, particularly preferred and very particularly preferred meanings of the radicals Z and X and also of index n listed in the general formulae (I) and (II) mentioned above are explained below. These preferred, particularly preferred and very particularly preferred meanings apply equally to all intermediates and end products which are mentioned in this description.

Z is preferably hydrogen, methyl, ethyl, propyl or isopropyl.

X is preferably halogen, $C_1$-$C_8$-alkyl, $C_1$-$C_8$-haloalkyl having up to 9 identical or different halogen atoms, $C_1$-$C_8$-alkoxy, $C_1$-$C_8$-haloalkoxy having up to 9 identical or different halogen atoms, carboxy, $C_3$-$C_7$-cycloalkyl or tri($C_1$-$C_8$-alkyl)silyl.

Moreover, two substituents X preferably form a 5- or 6-membered ring, as a result of which a bicycle selected from 1,3 -benzodioxolyl, 1,2,3,4-tetrahydroquinoxalinyl, 3,4-dihydro-2H-1,4-benzoxazinyl, 1,4-benzodioxanyl, indanyl, 2,3-dihydrobenzofuranyl or indolinyl is formed.

n is preferably 1, 2 or 3.

Z is particularly preferably hydrogen, methyl.

X is particularly preferably fluorine, chlorine, methyl, ethyl, propyl, isopropyl, tert-butyl, trifluoromethyl, difluoromethyl, methoxy, trifluoromethoxy, difluoromethoxy, trimethylsilyl, carboxy.

n is particularly preferably 1 or 2.

Z is very particularly preferably hydrogen.

X is very particularly preferably fluorine, chlorine, methyl, methoxy, isopropyl, tert-butyl, trifluoromethyl, trifluoromethoxy, trimethylsilyl, carboxy.

n is very particularly preferably 1.

According to the invention, it is thus intended that the desired substituted N-(benzyl)cyclopropanamines of the general formula (II) are prepared by a catalytic hydrogenation of the corresponding N-[(aryl) methylene]cyclopropanamine derivatives of the general formula (I). The desired substituted N-(benzyl)cyclopropanamines of the general formula (II) are obtained under the preferred reaction conditions according to the invention and specified in more detail below, with good yields in high purity, the process according to the invention thus overcoming the disadvantages specified above. The desired compounds are obtained here in a purity which generally renders extensive work-up of the direct reaction product unnecessary.

Within the context of the present invention, the term "alkyl", either on its own or in combination with further terms such as, for example, haloalkyl, is understood as meaning a radical of a saturated, aliphatic hydrocarbon group having 1 to 8 carbon atoms, which may be branched or unbranched. Examples of $C_1$-$C_8$-alkyl radicals are methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl, n-hexyl n-heptyl and n-octyl. From these alkyl radicals, $C_1$-$C_6$-alkyl radicals are particularly preferred. $C_1$-$C_4$-alkyl radicals are especially preferred.

According to the invention, the term "aryl" is understood as meaning an aromatic radical having 6 to 14 carbon atoms, preferably phenyl.

Within the context of the present invention, "radicals substituted by halogen" are understood as meaning, for example, haloalkyl, radicals halogenated one or more times up to the maximum possible number of substituents. In the event of polyhalogenation, the halogen atoms may be identical or different. Halogen here stands for fluorine, chlorine, bromine or iodine, in particular for fluorine, chlorine or bromine.

The term "alkoxy", either on its own or in combination with further terms such as, for example, haloalkoxy, is in the present case understood as meaning a radical O-alkyl, the term "alkyl" having the meaning above.

Optionally substituted radicals may be mono- or polysubstituted, where, in the case of a polysubstitution, the substituents may be identical or different.

The conversion of the N-[(aryl)methylene]cyclopropanamine derivatives of the general formula (I) to the corresponding amines of the general formula (II) is carried out by a catalytic hydrogenation [Process (A)]. The catalyst which may be used for the catalytic hydrogenation for reducing the compound of the general formula (I) is any desired hydrogenation catalyst. Suitable catalysts optionally comprise one or more metals of groups 8-10 of the Periodic Table of the Elements on an arbitrary customarily inorganic support. Of suitability are, for example, precious metal catalysts, such as ruthenium catalysts, palladium catalysts, platinum catalysts and rhodium catalysts, Raney nickel catalysts and Raney cobalt and Lindlar catalysts. However, besides these heterogeneous catalysts, hydrogenations can also be carried out over homogeneous catalysts, for example over the Wilkinson catalyst. The corresponding catalysts can be used in supported form, for example on carbon (carbon or activated carbon) Aluminium oxide, silicon dioxide, zirconium dioxide, calcium carbonate or titanium dioxide. Corresponding catalysts are known per se to the person skilled in the art. Particular preference is given to palladium catalysts. The catalysts can be used either in their damp form or dry form. The catalyst used is preferably reused for several reactions.

In the process (A) according to the invention, the catalyst is used in a concentration of from about 0.01 to abut 30% by weight, based on the imine of the formula (I) used. Preferably, the catalyst is used in a concentration o from about 0.01 to about 5% by weight, particularly preferably from about 0.1 to about 2.0% by weight.

The catalytic hydrogenation can be carried out under superatmospheric pressure in an autoclave or at atmospheric pressure in a hydrogen gas atmosphere. The hydrogen gas atmosphere can additionally also comprise inert gases, for example argon or nitrogen. The catalytic hydrogenation is carried out preferably at a temperature of form 10 to 200° C., particularly preferably at 10 to 150° C., very particularly preferably at 10 to 60° C. The hydrogen pressure is usually 0.1 to 50 bar, preferably 0.1 to 30 bar, particularly preferably 1 to 6 bar.

Further reagents used for the hydrogenation of imines and hydrogenation conditions are described in the publications by Harada, in Patai, "The Chemistry of the Carbon-Nitrogen Double Bond", pages 276 to 293; by Nishimura, "Handbook of Heterogeneous Catalytic Hydrogenation for Organic Synthesis"2, pages 226 to 250, John Wiley and Sons, New York, 2001 and by Rylander, "Catalytic Hydrogenation over Platinum Metals", pages 291 to 303, Academic Press, New York, 1967.

In general, it is advantageous to carry out the process (A) according to the invention for the hydrogenation of the imines in the presence of solvents (diluents). Solvents are advantageously used in an amount such that the reaction mixture remains readily stirrable throughout the entire hydrogenation process. Suitable solvents for carrying out the process according to the invention are all organic solvents that are inert under the reaction conditions, the type of solvent used depending on the way in which the reduction is carried out.

Examples to be mentioned are alcohols such as methanol, ethanol, isopropanol, butanol; ethers, such as ethyl propyl ether, methyl tert-butyl ether, n-butyl ether, anisole, phenetol, cyclohexyl methyl ether, dimethyl ether, diethyl ether, dimethyl glycol diphenyl ether, dipropyl ether, diisopropyl ether, di-n-butyl ether, diisobutyl ether, diisoamyl ether, ethylene glycol dimethyl ether, isopropyl ethyl ether, tetrahydrofuran, methyl tetrahydrofuran, dioxane, dichlorodiethyl ether and polyethers of ethylene oxide and/or propylene oxide; amines such as trimethyl-, triethyl-, tripropyl-, tributylamine, N-methylmorpholine, pyridine, alkylated pyridines and tetramethylenediamine; aliphatic, cycloaliphatic or aromatic hydrocarbons, such as pentane, n-hexane, n-heptane, n-octane, nonane and technical-grade hydrocarbons which may be substituted by fluorine and chlorine atoms, such as dichloromethane, trichloromethane, tetrachloromethane, fluorobenzene, chlorobenzene or dichlorobenzene; for example so-called white spirits with components having boiling points in the range for example from 40° C. to 250° C., cymene, benzine fractions within a boiling interval from 70° C. to 190° C., cyclohexane, methylcyclohexane, petroleum ether, ligroin, octane, benzene, toluene, chlorobenzene, bromobenzene, nitrobenzene, xylene; esters such as methyl, ethyl, butyl, isobutyl acetate, and also dimethyl, dibutyl, ethylene carbonate; and aliphatic alcohols, such as methanol, ethanol, n-propanol and isopropanol and n-butanol.

Of the aforementioned solvents, preference is given to alcohols, in particular methanol and ethanol, specifically methanol.

The reaction according to the invention as in process (A) can also be carried out without a diluent for N-[(aryl)methylene]cyclopropylamine derivatives of the formula (I) that are present in liquid form.

The amounts of solvents used when carrying out the process (A) according to the invention can be varied within a wide range. In general, solvent amounts in the range from 1 times to 50 times the amount of solvent, particularly preferably from 2 times to 40 times the amount of solvent, in particular from 2 times to 30 times the amount of solvent, in each case based on the N-[(aryl)methylene]cyclopropanamine derivative of the general formula (I) used, are used.

It was surprising to observe that under the particularly preferred reaction conditions of the process according to the invention, a hydrogenolysis of the cyclopropyl substituent is observed only to a very slight extent.

Work-up (purification) and isolation of the hydrogenated imines can take place, for example, by crystallization and/or distillation.

Moreover, the present invention also relates to the use of the compounds of the formula (I) for the preparation of compounds of the general formula (II), as is disclosed in the process described above.

The present invention also provides a process (B) for the preparation of the N-[aryl)methylene]cyclopropanamine derivatives of the general formula (I)

(I)

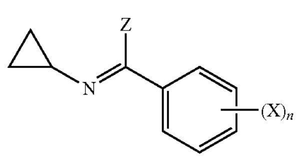

in which Z, X and n have the meanings given above, characterized in that cyclopropylamine is condensed with carbonyl compounds of the general formula (III)

(III)

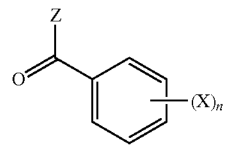

in which Z, X and n have the meanings given above.

The carbonyl compounds of the formula (III) required as starting materials for this process (B) are commercially available or can be prepared by processes known in the literature.

When carrying out process (B), an acid can optionally be added as catalyst. Examples thereof are acetic acid, p-toluolenesulphonic acid, trifluoroacetic acid. Acetic acid is preferably used. Acidic salts can also be used, e.g. $KHSO_4$ or $NaHSO_4$.

If corresponding catalysts are used, then their amount can be from 0.01 to 10 percent by weight, based on the cyclopropylamine used.

Moreover, process (B) can also be carried out such that the water which is formed during the reaction between amine and carbonyl compound of the formula (III) by condensation is removed from the reaction mixture. This is possible, for example, by using water-binding agents, for example sodium sulphate, magnesium sulphate or molecular sieve, or by using a device for separating off water. The hydrogenation can, however, also be carried out without removal of the water.

Process (B) can generally be carried out under reduced pressure, at atmospheric pressure or under superatmospheric pressure. The temperatures used can likewise vary, depending on the substrates used, and are easy for the person skilled in the art to ascertain through routine experiments. For example, the reaction for the preparation of the compounds of the general formula (I) can be carried out at a temperature of −20° C. to 200° C., preferably 10 to 100° C. Particular preference is given to carrying out the reaction at atmospheric pressure and temperatures of 10 to 100° C.

Moreover, process (B) can also be carried out in the presence of solvents (diluents). The solvents are also used in this process step preferably in an amount such that the reaction mixture remains readily stirrable throughout the entire process. Suitable solvents for carrying out the process according to the invention for the preparation of the imines of the general formula (I) are all organic solvents that are inert under the reaction conditions.

Examples are: alcohols such as methanol, ethanol, isopropanol, butanol; ethers, such as ethyl propyl ether, methyl tert-butyl ether, n-butyl ether, anisole, phenetol, cyclohexyl methyl ether, dimethyl ether, diethyl ether, dimethyl glycol diphenyl ether, dipropyl ether, diisopropyl ether, di-n-butyl ether, diisobutyl ether, diisoamyl ether, ethylene glycol dimethyl ether, isopropyl ethyl ether, tetrahydrofuran, dioxane, dichlorodiethyl ether and polyethers of ethylene oxide and/or propylene oxide; nitrocarbons such as nitromethane, nitroethane, nitropro- pane, nitrobenzene, chloronitrobenzene, o-nitrotoluene; nitriles such as acetonitrile, methylnitrile, propionitrile, butyronitrile, isobutyronitrile, benzonitrile, phenylnitrile, m-chlorobenzonitrile, and also compounds such as tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide, diisoamyl sulphoxide; sulphones such as dimethyl, diethyl, dipropyl, dibutyl, diphenyl, dihexyl, methylethyl, ethylpropyl, ethylisobutyl and pentamethylene sulphone; aliphatic, cycloaliphatic or aromatic hydrocarbons such as pentane, hexane, heptane, octane, nonane and technical-grade hydrocarbons, for example so-called white spirits with components having boiling points in the range for example from 40° C. to 250° C., cymene, benzine fractions within a boiling interval from 70° C. to 190° C., cyclohexane, methylcyclohexane, petroleum ether, ligroin, octane, benzene, toluene, nitrobenzene and xylene. Of the aforementioned solvents, particular preference is given xylene, cyclohexane and toluene.

In a further embodiment, the reaction between amine and the carbonyl compound of the formula (III) can also take place without a diluent.

If process (B) is carried out in a solvent, the solvent can be removed by distillation after the end of the reaction. This can take place under atmospheric pressure or reduced pressure at room temperature or elevated temperatures. However, the mixture can also be transferred directly to the hydrogenation, which is advantageous particularly from the point of view of economic considerations. In this embodiment of the process according to the invention, a work-up of the imine of the formula (I) is then dispensed with.

Moreover, the present invention further provides the N-[(aryl)methylene]cyclopropanamine derivative of the general formula (I)

(I)

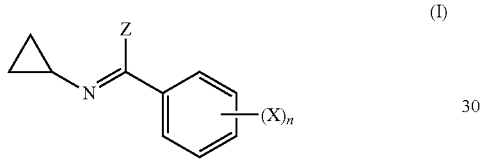

in which Z, X and n have the meanings given above, which are used as intermediates in the preparation of the N-(benzyl)cyclopropanamines of the general formula (II).

The present invention is illustrated by reference to the examples below, although he examples should not be interpreted in a manner which limits the invention.

PREPARATION EXAMPLES

General working instructions:

1.03 molar equivalents of cyclopropylamine are added dropwise to 1 equivalent of the aldehyde [carbonyl compound of the formula (III) in which Z is hydrogen]—a 1.80 molar solution in methanol—and stirred for one hour at room temperature. 0.09 mol % of a palladium catalyst on activated carbon are then added. After rendering the autoclave inert with nitrogen, 6 bar of hydrogen are injected and the reaction mixture is stirred at room temperature until the hydrogen absorption has finished. The catalyst is separated off by filtration and the solvent is removed by distillation.

Example 1

Synthesis of N-(3-Fluorobenzyl)Cyclopropanamine

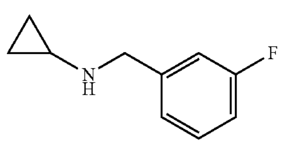 [SMILES: Fc1cccc(CNC2CC2)c1]

The reaction was carried out on a 0.072 molar scale. The hydrogen absorption was complete after five hours. The desired product was obtained in 91.8% yield. $^1$H-NMR ($CDCl_3$): 7.29-7.25 (m, 1H), 7.08 (d, 1H), 7.03 (dt, 1H), 6.93 (t, 1H), 3.82 (s, 2H), 2.14 (m, 1H), 2.01 (br s, 1H), 0.46 0.37 (m, 4H).

Example 2

Synthesis of Methyl 4-[(Cyclopropylamino)Methyl]benzoate

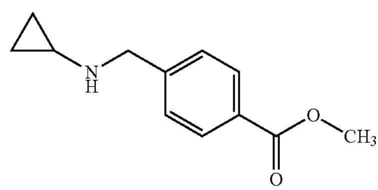

The reaction was carried out on a 0.072 molar scale. The hydrogen absorption was complete after five hours. The desired product was obtained in 80.4% yield.

$^1$H-NMR ($CDCl_3$): 7.99 (d, 2H), 7.38 (d, 2H), 3.90 (s, 3H), 3.89 (s, 2H), 2.40 (br s, 1H), 2.20-2.12 (m, 1H), 0.46-0.37 (m, 4H).

Example 3

Synthesis of N-(1-Naphthylmethyl)Cyclopropanamine

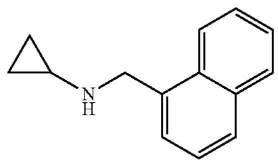 [SMILES: c1ccc2c(CNC3CC3)cccc2c1]

The reaction was carried out on a 0.072 molar scale. The hydrogen absorption was complete after nine hours.

The desired product was obtained in 80.4% yield.

$^1$H-NMR ($CDCl_3$): 8.11 (d, 1H), 7.85 (dd, 1H), 7.75 (d, 1H), 7.54-7.40 (m, 4H), 4.29 (s, 2H), 1.93 (br s, 1H), 2.22 (m, 1H), 0.49-0.44 (m, 4H).

Example 4

Synthesis of N-(2-Isopropylbenzyl)Cyclopropanamine

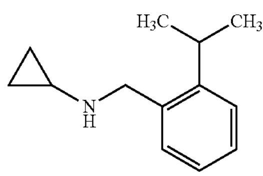

The reaction was carried out on a 0.129 molar scale. The hydrogen absorption was complete after four hours.

The desired product was obtained in 91.9% yield.

$^1$H-NMR ($CD_3CN$): 7.29 (dd, 1H), 7.25 (dd, 1H), 7.22-7.19 (m, 1H), 7.12 7.09 (m, 1H), 3.82 (s, 2H), 3.32-3.29 (m, 1H), 2.15-2.12 (m,1H), 1.93 (br s, 1H), 1.20 (d, 6H), 0.40-0.38 (m, 2H), 0.28-0.27 (m, 2H).

Example 5

Synthesis of N-(4-Methylbenzyl)Cyclopropanamine

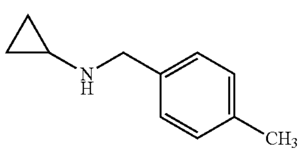

The reaction was carried out on a 0.073 molar scale. The hydrogen absorption was complete after seven hours. The desired product was obtained in 83.3% yield.

$^1$H-NMR ($CDCl_3$): 7.18 (d, 2H), 7.11 (d, 2H), 3.78 (s, 2H), 2.32 (s, 3H), 2.14-2.10 (m, 1H), 1.85 (br s, 1H), 0.44-0.36 (m, 4H).

Example 6

Synthesis of N-(4-Tert-Butylbenzyl)Cyclopropanamine

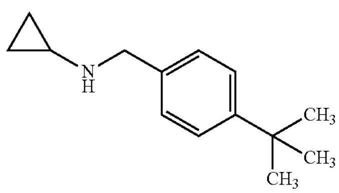

The reaction was carried out on a 0.049 molar scale. The hydrogen absorption was complete after three hours. The desired product was obtained in 90.8% yield.

$^1$H-NMR ($CDCl_3$): 7.33 (d, 2H), 7.24 (d, 2H), 3.82 (s, 2H), 3.15 (br s, 1H), 2.19-2.15 (m, 1H), 1.30 (s, 9H), 0.45-0.42 (m, 4H).

Example 7

Synthesis of N-(4-Methoxybenzyl)Cyclopropanamine

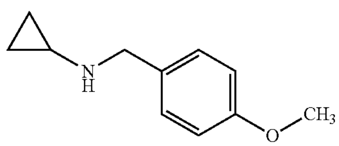

The reaction was carried out on a 0.072 molar scale. The hydrogen absorption was complete after six hours. The desired product was obtained in 88.6% yield.

$^1$H-NMR ($CDCl_3$): 7.21 (d, 2H), 6.85 (d, 2H), 3.78 (s, 3H), 3.76 (s, 2H), 2.14-2.10 (m, 1H), 1.78 (br s, 1H), 0.44-0.36 (m, 4H).

Example 8

Synthesis of N-(2,4-Dimethylbenzyl)Cyclopropanamine

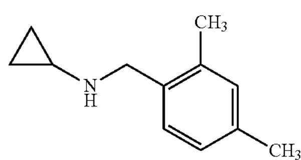

The reaction was carried out on a 0.037 molar scale. The hydrogen absorption was complete after two hours.

The desired product was obtained in 88.6% yield. $^1$H-NMR ($CDCl_3$): 7.13 (d, 1H), 6.96 (s, 1H), 6.95 (s, 1H), 3.79 (s, 2H), 2.31 (s, 4H, $CH_3$+NH), 2.28 (s, 3H), 2.17-2.14 (m, 1H), 0.45-0.39 (m, 4H).

Example 9

Synthesis of N,N-lbenzene-1,4-diylbis(methylenaldi-cyclopropanamine

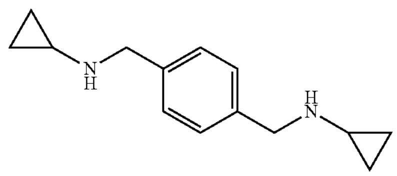 [SMILES: c1cc(CNC2CC2)ccc1CNC1CC1]

The reaction was carried out on a 0.037 molar scale. As a departure from the general working instruction, 2.06 equivalents of cyclopropylamine were added, based on the terephthalaldehyde. The hydrogen absorption was complete after 14 hours. The product was obtained in 88.1% yield.

$^1$-HNMR ($CDCl_3$): 7.20 (d, 2H), 7.13 (d, 2H), 3.82 (s, 4H), 2.15-2.12 (m, 2H), 1.79 (br s, 2H), 0.44-0.37 (m, 8H).

The invention claimed is:

1. A process for the preparation of N-(benzyl)cyclopropanamines of the general formula (II)

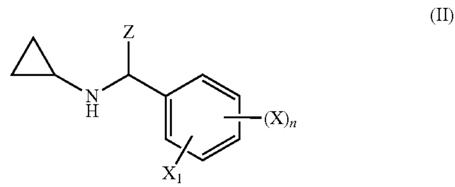

(II)

wherein

Z is hydrogen, $C_1$-$C_8$-alkyl, $C_1$-$C_4$-haloalkyl or $C_3$-$C_7$-cycloalkyl, $X_1$ is halogen or $C_1$-$C_8$-haloalkyl having up to 9 identical or different halogen atoms, X is $C_1$-$C_8$-alkyl or $C_1$-$C_8$-haloalkyl having up to 9 identical or different halogen atoms, n is 1, 2, 3, or 4, wherein N-[(aryl)methylene]cyclopropanamine compounds of the general formula (I)

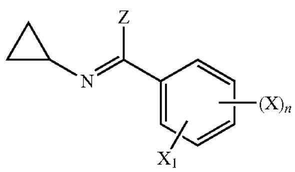

in which Z, X, $X_1$ and n have the meanings given above, are catalytically hydrogenated.

2. The process according to claim 1, wherein a hydrogenation catalyst that is used is selected from the group consisting of a precious metal catalyst and a Wilkinson catalyst.

3. The process according to claim 1, wherein a hydrogenation catalyst that is used is selected from the group consisting of a ruthenium catalyst, a palladium catalyst, a platinum catalyst, a rhodium catalyst, a Raney nickel catalyst, a Raney cobalt catalyst, a Lindlar catalyst, and a Wilkinson catalyst.

4. The process according to claim 2, wherein the catalyst is used in supported form applied to carbon, activated carbon, aluminium oxide, silicon dioxide, zirconium dioxide, calcium carbonate or titanium dioxide.

5. The process according to claim 3, wherein the catalyst is used in supported form applied to carbon, activated carbon, aluminium oxide, silicon dioxide, zirconium dioxide, calcium carbonate or titanium dioxide.

6. The process according to claim 1, wherein the catalyst is used in a concentration of about 0.01% to about 30% by weight.

7. The process according to claim 2, wherein the catalyst is used in a concentration of about 0.01% to about 30% by weight.

8. The process according to claim 3, wherein the catalyst is used in a concentration of about 0.01% to about 30% by weight.

9. The process according to claim 4, wherein the catalyst is used in a concentration of about 0.01% to about 30% by weight.

10. The process according to claim 5, wherein the catalyst is used in a concentration of about 0.01% to about 30% by weight.

11. A process for the preparation of N-(benzyl)cyclopropanamines of the general formula (II)

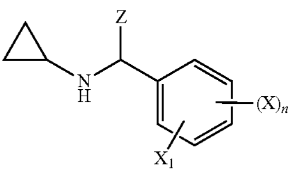

wherein

Z is hydrogen, $C_1$-$C_8$-alkyl, $C_1$-$C_4$-haloalkyl or $C_3$-$C_7$-cycloalkyl, $X_1$ is halogen or $C_1$-$C_8$-haloalkyl having up to 9 identical or different halogen atoms, X is $C_1$-$C_8$-alkyl or $C_1$-$C_8$-haloalkyl having up to 9 identical or different halogen atoms, n is 1, 2, 3, or 4, wherein, in a first step [process (B)], cyclopropylamine is condensed with carbonyl compounds of the general formula (III)

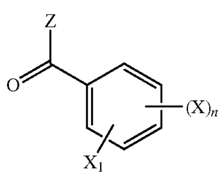

wherein Z, X, $X_1$ and n have the meanings given above, and the resulting N-[(aryl)methylene]cyclopropanamine compounds of the general formula (I)

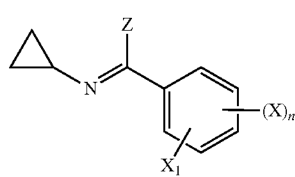

wherein Z, X, $X_1$ and n have the meanings given above, are catalytically hydrogenated in a second step [process (A)].

12. N-[(Aryl)methylene]cyclopropanamine compounds of the general formula (I)

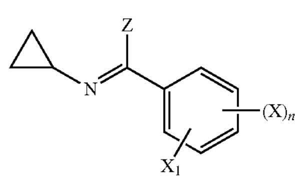

wherein

Z is hydrogen, $C_1$-$C_8$-alkyl, $C_1$-$C_4$-haloalkyl or $C_3$-$C_7$-cycloalkyl, $X_1$ is halogen or $C_1$-$C_8$-haloalkyl having up to 9 identical or different halogen atoms, X is $C_1$-$C_8$-alkyl or $C_1$-$C_8$-haloalkyl having up to 9 identical or different halogen atoms, n is 1, 2, 3, or 4.

* * * * *